US010041911B2

(12) United States Patent
Bonadies, Jr. et al.

(10) Patent No.: US 10,041,911 B2
(45) Date of Patent: Aug. 7, 2018

(54) METHODS AND SYSTEMS FOR MEASURING CORROSION IN-SITU

(71) Applicant: DOW GLOBAL TECHNOLOGIES, LLC, Midland, MI (US)

(72) Inventors: Joseph Bonadies, Jr., Midland, MI (US); Gretchen Baier, Midland, MI (US); J. D. Tate, Freeport, TX (US); Patrick M. Russell, Freeland, MI (US)

(73) Assignee: Dow Global Technologies LLC, Midland, MI (US)

( * ) Notice: Subject to any disclaimer, the term of this patent is extended or adjusted under 35 U.S.C. 154(b) by 122 days.

(21) Appl. No.: 14/894,515

(22) PCT Filed: May 27, 2014

(86) PCT No.: PCT/US2014/039529
§ 371 (c)(1),
(2) Date: Nov. 28, 2015

(87) PCT Pub. No.: WO2014/193808
PCT Pub. Date: Dec. 4, 2014

(65) Prior Publication Data
US 2016/0109413 A1    Apr. 21, 2016

Related U.S. Application Data

(60) Provisional application No. 61/827,975, filed on May 28, 2013.

(51) Int. Cl.
*G01N 29/04* (2006.01)
*G01N 29/22* (2006.01)
(Continued)

(52) U.S. Cl.
CPC ............ *G01N 29/07* (2013.01); *G01N 17/006* (2013.01); *G01N 17/04* (2013.01); *G01N 17/043* (2013.01);
(Continued)

(58) Field of Classification Search
CPC .. G01N 29/07; G01N 29/223; G01N 29/2475; G01N 29/4427; G01N 17/006;
(Continued)

(56) References Cited

U.S. PATENT DOCUMENTS 3,156,887 A * 11/1964 Weikal .................. G01N 17/00
                                                              174/77 R
3,639,876 A *  2/1972 Wilson .................. G01N 17/02
                                                              174/152 GM
(Continued)

FOREIGN PATENT DOCUMENTS

GB        2238120 A     5/1991
WO    2009141135 A1    11/2009

OTHER PUBLICATIONS

International Search Report for PCT/US2014/039529 dated Aug. 6, 2014.
(Continued)

*Primary Examiner* — J M Saint Surin
(74) *Attorney, Agent, or Firm* — McDonnell Boehnen Hulbert & Berghoff LLP (57) ABSTRACT

Systems and methods for measuring corrosion rate of an equipment material are provided. A system may comprise a corrosion probe body for insertion within an interior of the equipment through which corrodant fluid flows. At least one sensor on the corrosion probe body includes an ultrasonic source configured to provide an ultrasonic signal into the probe body material, and a receiver configured to receive reflections of the ultrasonic signal from the probe body (Continued)

material and generate electrical response signals indicative of the travel time of the ultrasonic signal. A heat exchanger may be placed in fluid communication with the probe body to deliver heated or cooled fluids to the probe body. A processor is configured to process the electrical response signals and produce corresponding corrosion data.

12 Claims, 4 Drawing Sheets

(51) Int. Cl.
  *G01N 29/24* (2006.01)
  *G01N 17/00* (2006.01)
  *G01N 17/04* (2006.01)
  *G01N 29/07* (2006.01)
  *G01N 29/44* (2006.01)

(52) U.S. Cl.
  CPC ......... *G01N 29/043* (2013.01); *G01N 29/223* (2013.01); *G01N 29/2475* (2013.01); *G01N 29/4427* (2013.01); *G01N 2291/011* (2013.01); *G01N 2291/0258* (2013.01); *G01N 2291/02854* (2013.01); *G01N 2291/044* (2013.01)

(58) Field of Classification Search
  CPC .... G01N 17/04; G01N 29/043; G01N 17/043; G01N 2291/044; G01N 2291/02854; G01N 2291/011; G01N 2291/0258
  USPC .......................................................... 73/655
  See application file for complete search history.

(56) References Cited

U.S. PATENT DOCUMENTS

| | | | | |
|---|---|---|---|---|
| 4,097,341 A | * | 6/1978 | Schell | G01N 17/00 165/11.1 |
| 4,098,662 A | * | 7/1978 | Schell | G01N 17/00 165/11.1 |
| 4,262,247 A | * | 4/1981 | Olson | G01N 17/00 324/700 |
| 4,585,542 A | * | 4/1986 | Wright | G01N 27/404 165/177 |
| 6,357,470 B1 | * | 3/2002 | Evans | F16L 41/16 137/315.01 |
| 7,249,628 B2 | * | 7/2007 | Pillion | F28D 7/08 165/11.1 |
| 8,629,688 B2 | * | 1/2014 | Chu | G01N 17/002 324/699 |
| 2002/0078752 A1 | | 6/2002 | Braunling et al. | |
| 2011/0067497 A1 | | 3/2011 | Grubb et al. | |

OTHER PUBLICATIONS

"Technical Information Compilation of Shanghai Industrial Equipment Innovation Exhibition," Shanghai Industrial Equipment Innovation Exhibition, pp. 221-223, Shanghai Production Technology Bureau, Shanghai Science and Technology Association, May 31, 1965.

"Ultrasonic Flaw Detecting Technology and Flaw Detector," pp. 222-224, National Defense Industry Press, Sep. 30, 1979.

"Heavy Castings and Forgings and Structural Ultrasonic Flaw Detection," Zhao Huangpei et al., pp. 78-79, Metallurgical Industry Press, Jan. 31, 2012.

* cited by examiner

METHODS AND SYSTEMS FOR MEASURING CORROSION IN-SITU

CROSS-REFERENCE TO RELATED APPLICATION

This application is a U.S. national phase of International Application No. PCT/US2014/039529, filed May 27, 2014, which claims priority from U.S. Provisional Application No. 61/827,975, filed May 28, 2013; the disclosures of both of these applications are incorporated herein by reference in their entireties.

BACKGROUND

Proper maintenance of process equipment used for manufacturing, shipment, storage, and various handling procedures is important for the equipment to operate reliably, safely, and economically. Often the integrity of process equipment is monitored to detect any corrosion or other degradation. The need to monitor process equipment integrity becomes more acute when the equipment is subjected to a highly corrosive environment or when the process equipment contains especially hazardous materials. Such an environment may result from aggressive processes such as chlorine, oxidizer, acid, and/or base manufacturing, or other such processes that are known to pose challenges to operators to avoid destroying process equipment and/or loss of containment. Quick and accurate assessments of corrosion of a material in a highly corrosive environment is thus useful in maintaining reliable and safe operation of the equipment and in some cases is required by law.

Monitoring techniques have been used to determine an average corrosion rate for a material over an extended period of time. Some monitoring techniques, such as those using ultrasonic technology, perform a determination of corrosion from outside the process equipment, e.g., thickness measurements are used to infer metal loss, and thus the amount of degradation or corrosion. Determining an average corrosion rate over an extended period of time does not provide real-time information regarding the degradation of a material, however. Rather it is the integration of a number of corrosion events over time. Furthermore, determining the corrosion from outside the process equipment may compromise accuracy of the estimated corrosion condition inside the equipment. These ex-situ methods often also involve placing personnel near the measurement point, sometimes at high elevations within the process equipment, which can place the personnel in a dangerous situation.

Electrical resistance (ER) probes have been used to measure a corrosion rate inside the process equipment. ER probes use a highly deformed piece of metal of a composition similar to the material of interest, and determine a corrosion rate of the target material based on proportionality of the change in resistance of the deformed metal to the corrosion of the target material. ER probes are highly sensitive to temperature change, resulting in poor accuracy. Further, ER probes are generally very thin, which both limits the dynamic range of measurement and results in a short sensor life. Highly deformed metals also corrode differently than metals of the same composition, but with less mechanical deformation. Additionally, ER probes do not address non-conductive materials.

Coupons have also been used for corrosion monitoring inside process equipment. A coupon is a small piece of metal, which is attached to the inside of the process equipment. The mass of a coupon is determined prior to and after exposure to a corrosive environment over a long period of time (nominally years). The estimated corrosion rate is thus the integration of corrosion events over a period of time; singular corrosion events are not identified. One difficulty in using coupons is the need to remove adherent corrosion products from the exposed coupon, prior to final weighing. One needs to be careful that the removal process does not bias the end result. Additionally, a coupon may be consumed without any indication prior to removal and inspection. Without real-time corrosion measurement capability, it is difficult to make improvements or to identify process variables related to the corrosion event.

Electrochemical devices have also been used for corrosion monitoring inside process equipment. Typically, corrosion of metals is electrochemical in nature, so the corrosion rate may be measured by use of electrochemistry, e.g., the transfer of electrons from a cathode to an anode. This process assumes the corrosion mechanism and a voltage/current, V/I, are both known, and these assumptions are easily incorrect because of complexity in electrochemical calculations.

SUMMARY

In accordance with the present invention, a system and a method are defined for measuring corrosion rate of an equipment material. In one embodiment, the system may comprise a corrosion probe body for insertion within an interior of the equipment through which corrosive fluid flows, wherein the corrosion probe body comprises a material substantially identical (with regard to chemistry and metallurgical history) to that of the equipment material. The system may further comprise at least one sensor on the corrosion probe body that includes an ultrasonic source configured to provide an ultrasonic pulse into the probe body material, and a receiver configured to receive reflections of the ultrasonic pulse from the probe body material and generate electrical response signals indicative of the travel time of the ultrasonic pulse, a processor configured to process the electrical response signals and produce corresponding metal thickness data, and a communication unit to communicate the corresponding corrosion data to a display on an exterior surface of the material.

The system may further include a heat exchanger in fluid communication with an annulus of the probe body and a temperature sensor to indicate the temperature of the probe body.

In another embodiment, a method for detecting a corrosion condition of a corrodible material in a corrosive environment is provided. The method comprises inserting a corrosion probe into the corrosive environment, wherein the corrosion probe comprises a probe body comprised of a material substantially identical to that of the corrodible material and a sensor attached to the probe body that is capable of projecting and receiving ultrasonic signals, projecting ultrasonic signals from the sensor to the probe body, receiving reflected ultrasonic signals with the sensor, generating electrical response signals that correspond to the reflected ultrasonic signals, processing the electrical response signals to indicate a corrosion condition of the material, and communicating the corrosion condition.

The system and method may be used for detection of a singular corrosion event, monitoring an amount of corrosion or degradation of equipment over time, and/or monitoring an integrated corrosion rate of a material. The method may be performed in a continuous manner so as to provide continuous, real-time measurements of a corrosion rate and corrosion events.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1:
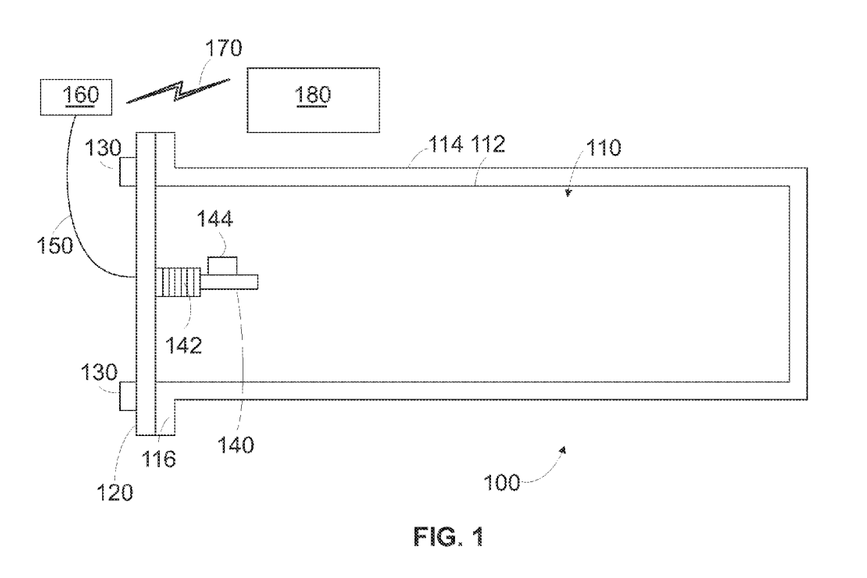
FIG. 1 depicts a schematic of an exemplary system in use with process equipment in accordance with at least one embodiment.

FIG. 1 depicts a schematic of an exemplary system 100 in use with process equipment in accordance with at least one embodiment. The system 100 may be used, among other things, to measure a corrosion rate of an equipment material within a corrosive environment. The system 100 provides for the ability to measure a corrosion rate and corrosion events for a material in real-time and in-situ. This can be particularly helpful during process upsets, as the damage to process equipment can be estimated in real-time and steps can be quickly taken to mitigate damage or loss of containment of a fluid within the process equipment.

In FIG. 1, the system 100 may include equipment such as a pipe 110 comprising an interior surface 112 and an exterior surface 114, a disk 120, fasteners 130, a corrosion probe 140, circuitry 150, a processor 160, communication links 170, and a display 180.

The system 100 may be implemented for use with corrosion monitoring and control for various processes. For example, the system 100 may be implemented for use with a chlorinated organics process, enhanced oil recovery, high-temperature processes (e.g., thermal treatment units, electrical power generation, large scale fired equipment, furnaces, fired-heaters, etc.). Other processes may include halogen substituted organics, corrosive gaseous products, steam, or corrosive solids.

The pipe 110 is a representative piece of process equipment and may be made from a metal, a polymer (e.g., plastic, rubber, etc.), a ceramic (e.g., concrete, brick, etc.), or a composite material comprising two or more materials with different properties. In other example embodiments, other process equipment components may be monitored, for example, vessels, tanks, and various other containers. The pipe 110 is exposed to a corrosive environment, such as a fluid (e.g., a gas or liquid) that degrades any exposed pipe material over time, deteriorating the physical properties of the material. In the system 100, a corrosive fluid flows through the pipe 110 and thus the interior surface 112 of the pipe 110 is exposed to the corrosive fluid.

Degradation of the pipe 110 material can lead to weakening of the material due to a loss of cross-sectional area. If the pipe material is a metal, degradation may also cause cracking of the material due to hydrogen embrittlement, for example. If the pipe material is a polymer, degradation may cause dimensional change and even cracking. It is important to maintain the structural integrity of the pipe 110, or any other such process equipment, so that the pipe 110 can operate reliably, safely, and economically.

A disk 120 may be mounted to a flange 116 on the pipe 110 with fasteners 130, and may extend across an opening of the equipment 110. Fasteners 130 may be bolts, screws, rivets, welds, braze material, or solders, for example. The disk 120 may include an opening, well, or other such female coupling part that allows for the insertion of the corrosion probe 140. In some example embodiments, the disk 120 may contain holes to allow for fluid flow therethrough.

The corrosion probe 140 may include at least one ultrasonic (UT) sensor that is configured to identify thickness changes in a material in-situ. In the example system 100, the corrosion probe 140 comprises a screw thread 142 to attach to a corresponding screw threaded opening in the disk 120. A heat exchanger 144 may be connected to the corrosion probe 140 to receive and deliver heated or cooled fluids to and from the corrosion probe 140. The heat exchanger 144 thus serves to heat or cool the corrosion probe 140 as desired. Further exemplary details regarding the structure of a corrosion probe such as the corrosion probe 140 are shown and described in further detail with respect to FIG. 2.

In some example embodiments, the corrosion probe 140 may attach directly to a flange or other protrusion from the pipe 110, and thus no additional disk piece would be required for attachment.

The described corrosion probe 140 measures the thickness of the containment as a function of time by measuring the time of flight that a sound wave requires to transport across the thickness and the reflection return. This time of flight is translated into a thickness. Electrical signals indicating the thickness are sent via the circuitry 150 to a processor such as the processor 160. The processor 160 performs the calculations from the speed of sound in that material at that temperature. The ultrasonic sensor generates time in and time out data for the processor 160.

Circuitry 150 connects the corrosion probe 140 to the processor 160. The circuitry may be electrical wiring, and may comprise one or more cables. A junction may connect the circuitry 150 to the corrosion probe 140. The circuitry 150 transmits electrical signals from the corrosion probe 140 to the processor 160 for processing and analysis. An additional cable may serve to provide power to operate the probe 140 from an external power source.

The processor 160 may be included on a tangible, non-transitory computer readable medium, and may perform functions in any of the processes or methods described herein. The processor 160 receives signals from the corrosion probe 140 via the circuitry 150 and sends a generated output to a display such as the display 180 or other indicator.

Communication links 170 between the processor and the display 180 may include wired connections, such as 4-20 mA analog signals, or a digital serial or parallel bus. Communication links 170 may also be wireless links, which may include Bluetooth, IEEE 802.11 (IEEE 802.11 may refer to IEEE 802.11-2007, IEEE 802.11n-2009, or any other IEEE 802.11 revision), or other wireless based communication links. The circuitry 150 may include the same wired or wireless technologies.

The display 180 may include a display screen 180 for visual output, in some example embodiments. In other example embodiments, the display may include an audio indicator. In some embodiments, the system 100 may not include any display element.

The system 100 allows for placement of the corrosion probe 140 in-situ, within the pipe 110. Such placement allows for reproducible and accurate corrosion measurements because the reading of the sensor is indicative of the conditions within the process, and is not confounded by variables ex-situ that are not related to the corrosive properties of the process. Moreover, the corrosion probe 140 is not in contact with the interior surface 112 of the pipe 110 but is located away from the pipe surface (equipment wall), allowing for a more targeted location to be monitored. In one example embodiment, the corrosion probe 140 may be located towards an exit of a heat-exchanger tube to monitor corrosion at that location. Ex-situ measurements are only relevant at the exterior wall of equipment and outside of the equipment, not inside the process.

Figure 2:
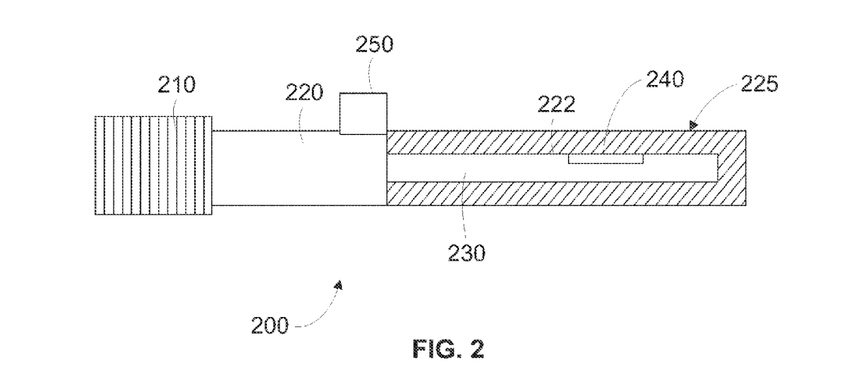
FIG. 2 depicts an example corrosion probe for use with the exemplary system of FIG. 1 in accordance with at least one embodiment.

FIG. 2 depicts an example corrosion probe 200 for use with the exemplary system 100 of FIG. 1, in accordance with at least one embodiment. The corrosion probe 200 may serve as the corrosion probe 140 in the system 100, for example.

The corrosion probe 200 includes a fastening portion 210 and a body portion 220. A cross-sectional portion 225 is taken from the body portion 220, revealing an annulus within the body portion 220 comprising at least one channel 230 and at least one sensor 240. A heat exchanger 250 may be attached to the corrosion probe 200 and may be in fluid communication with the at least one channel 230.

The fastening portion 210 is configured to attach with a corresponding fastening element to be placed within the process equipment, such as described with reference to FIG. 1. The fastening portion 210 may include a screw thread, such as a 19 mm or 25.4 mm normal pipe thread fitting, for example. In another example, the fastening portion 210 may include a flange with holes for bolt insertion. Other fastening means may also be envisioned.

The body portion 220 may be made from a pipe. In one example embodiment, the pipe may comprise a thickness of at least 3.175 mm. For example, the pipe may be schedule 40 steel pipe, 50.8 mm size, with a wall thickness of about 3.92 mm+/−0.051 mm. Such a thick pipe allows for a long service life, particularly when exposed to high corrosion events. The thickness also allows for the annulus of the body portion 220 to remain open instead of having to be filled to prevent structural collapse of the probe. By allowing the annulus to remain open, the hollow channel 230 is able to provide for heating and cooling of the corrosion probe 200, as will be described in further detail below. The body portion 220 is preferably made from the same material or a material similar to the material of the process equipment within which the body portion 220 is placed. The body portion 220 may comprise non-electrical conductive material. The speed of sound for the material comprising the body portion 220 is thus known, which provides high accuracy when calculating corrosion data from received sensor 240 signals.

The sensor 240 may be positioned at a machined section of the body portion 220, allowing the sensor 240 to contact an interior face 222 of the body portion 220. (The machined section refers to a portion of the interior face 222 of the body portion 220, which has been machined to create a smooth surface on the interior face 222 that will not interfere with the corrosion determination.) In the example embodiment of FIG. 2, the sensor 240 is an ultrasonic transducer. There are two connections to the sensor 240, one to transmit an ultrasonic signal through the body portion 220, and one to detect the reflected ultrasonic signals. The time of flight of the ultrasonic signal is related to the thickness of the material of the body portion 220.

The sensor 240 may be located near or at the distal end of the probe body 220 in some example embodiments.

In some embodiments, the corrosion probe 200 may comprise a plurality of sensors 240. There may be, for example, a first sensor and a second sensor.

The thickness of a manufactured pipe tends to be very consistent. Thus, the initial thickness of the pipe can be measured prior to installation in the system. Such a measurement provides conformation of operability of the probe and of initial calibrations. Changes as small as 0.00254 mm can be measured by the system. For each type or design of manufactured pipe, there is a calculated minimum thickness necessary to provide safe containment of the process fluid. The minimum thickness is a function of temperature and pressure. For example, using a 50.8 mm low carbon steel (SA-106 Grade B) pipe, Schedule 40 the safe temperature and pressure maximums are shown in Table 1. For any alloy, a similar table of safe operating temperatures/pressures is known.

TABLE 1

| Material | Pressure (MPa) | | | | | | |
| --- | --- | --- | --- | --- | --- | --- | --- |
| SA-106 Gr. B | 204.4° C. 400° F. 8.964 | 260° C. 500° F. 8.964 | 315.6° C. 600° F. 8.964 | 371.1° C. 700° F. 7.729 | 426.7° C. 800° F. 5.516 | 482.2° C. 900° F. 3.103 | 437.8° C. 1000° F. 1.034 |

The corrosion probe 140, when inserted into the corroding medium, can measure a change in thickness from the initial reading, allowing the user to calibrate thickness versus temperature. In one embodiment, the corrosion probe 140 includes a first sensor and a second sensor. In this embodiment, the first sensor has a first focal plane (also called a focal point) located at a first probe thickness and the second sensor has a second focal plane located at a second probe thickness. A focal plane represents the area orthogonal to the sensor axis where the ultrasonic signal is focused, which is an optimization of the send and receive angles for the sensor. The accuracy/precision of the corrosion determination is best within the focal plane. The first probe thickness may be the initial thickness of the probe wall and the second probe thickness may be the minimum thickness of the probe wall. Using the probe in this manner allows the user to detect when the minimum thickness has been reached and thus provide efficient and safe operating conditions.

Figure 5:
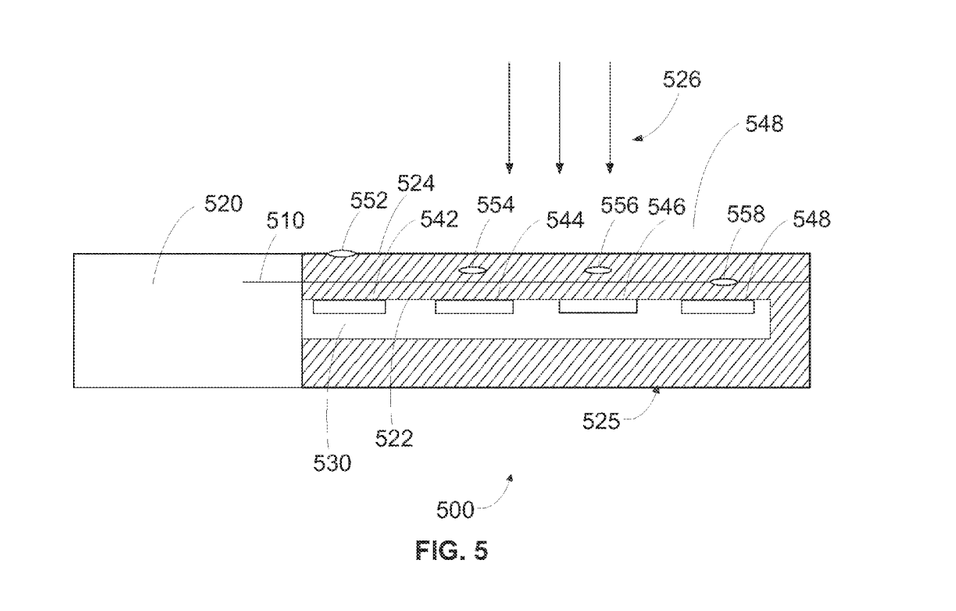
FIG. 5 depicts an example corrosion probe for use with the exemplary system of FIG. 1 in accordance with at least one embodiment.

FIG. 5 depicts an example corrosion probe 500 for use with the exemplary system 100 of FIG. 1, in accordance with at least one embodiment. The corrosion probe 500 may serve as the corrosion probe 140 in the system 100, for example. A cross-sectional portion 525 is taken from a body portion 520, revealing an annulus within the body portion 520 comprising at least one channel 530 and a plurality of sensors 542, 544, 546, and 548 in contact with an interior face 522 of the body portion 520, opposite of an exterior face 524 of the body portion 520. A process fluid 526 contacts the exterior face 524. Each sensor may have a focal plane at a set distance from the sensor within the wall of the body portion 520. This distance is calibrated for each sensor.

The corrosion probe 500 in this embodiment includes a first sensor 542 and a first focal plane 552, a second sensor 544 and a second focal plane 554, a third sensor 546 and a third focal plane 556, and a fourth sensor 548 and a fourth focal plane 558. The first focal plane 552 is located at an initial thickness, the second focal plane 554 and the third focal plane 556 are located at an intermediate thickness, and the fourth focal plane 558 is located at a minimum thickness 510. The minimum thickness 510 for the type of pipe used may be determined as discussed above.

The first sensor 552 determines the initial corrosion rate in a system. The second sensor 554 and the third sensor 556 are redundant and enable the use of statistics to remove intrinsic variation between individual sensors and variation due to random surface features of the probe body 520. The fourth sensor 558 alerts the user when the minimum thickness of the pipe is reached.

In another embodiment, the system may be used to evaluate erosion-enhanced corrosion (which occurs when the corrosion fluid has a high flow velocity and includes solid particles) by evaluating corrosion at opposite sides of the piping (i.e., upstream and downstream). In this embodiment, the relative flow velocity of the erosion fluid is higher at one surface than at the other and thus, the solid particles contact this surface at a higher flow velocity than the opposite surface. Thus, the first sensor is located on a side of the corrosion probe body opposite of the second sensor in order to determine how corrosion is enhanced by variations of the flow velocity.

Figure 6:
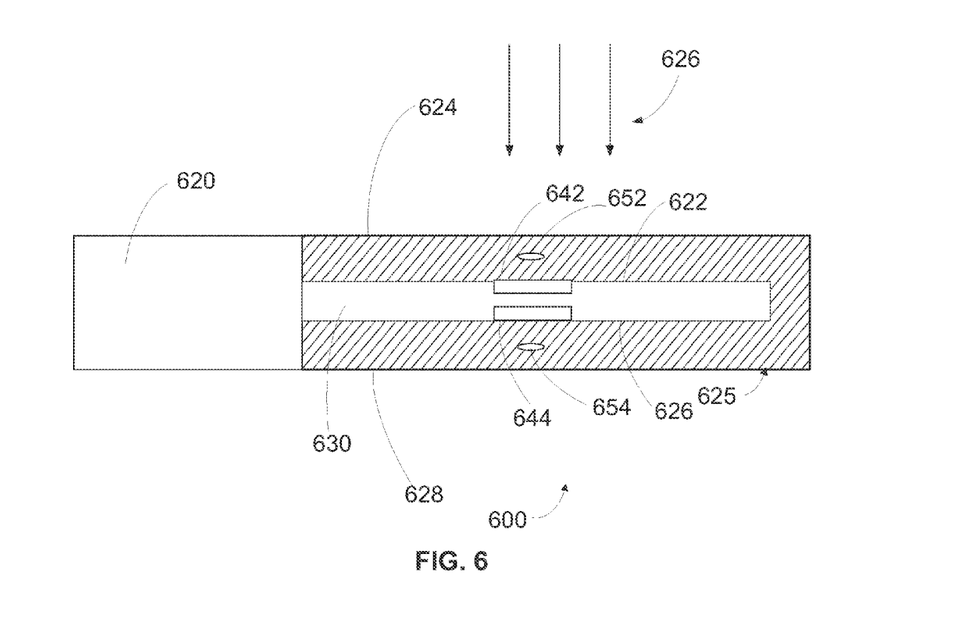
FIG. 6 depicts an example corrosion probe for use with the exemplary system of FIG. 1 in accordance with at least one embodiment.

FIG. 6 depicts an example corrosion probe 600 for use with the exemplary system 100 of FIG. 1, in accordance with at least one embodiment. The corrosion probe 600 may serve as the corrosion probe 140 in the system 100, for example. A cross-sectional portion 625 is taken from a body portion 620, revealing an annulus within the body portion 620 comprising at least one channel 630 and at least two sensors 642 and 644. The first sensor 642 is in contact with a first interior face 622 of the body portion 620, opposite of an upstream exterior face 624 of the body portion 620. A process fluid 626 contacts the upstream exterior face 624. The first sensor 642 has a first focal plane 652. The second sensor 644 is in contact with a second interior face 626 of the body portion 620, opposite of a downstream exterior face 628 of the body portion 620. The second sensor 644 has a second focal plane 654. The first sensor 642 and the second sensor 644 may be oriented 180 degrees apart, such that first sensor 642 is facing the incoming process fluid 626 and the second sensor 644 is facing away from the incoming process fluid. In some embodiments, the first sensor 642 and the second sensor 644 may located directly across from one another in the channel 630. In other embodiments, the first sensor 642 may be located above the second sensor 644, but close enough that the results are not biased to depth.

A probe surface may be heterogeneous in nature, especially if it has experienced the effects of corrosion (e.g., pits, cracks, dips, peaks, etc.). Thus, variability in readings from a single probe may be the results of such surface defects, not the corrosion rate. The use of multiple sensors/ultrasonic sources lessens the uncertainty associated with a surface profile and provides means to determine average readings from multiple sensors on a single probe body.

Corrosion generally dissolves metal at a constant rate; however, because most alloys are non-homogenous, corrosion occurs with anodes and cathodes on the same metal. Thus, the metal may thin inconsistently. By employing a plurality of sensors, specific anomalies such as pitting, cracking, under deposit corrosion, and crevices, may be detected.

Changes in spatial relationships are another source of variability in ultrasonic detection of existing methods. A plurality of sensors 240 may be located in fixed positions and thus able to consistently evaluate thickness because the composition, composition distribution, the velocity, and the number of reflections at that location remain unchanged. For example, a first sensor may be located at a first location on the corrosion probe body and a second sensor may be located at a second location on the corrosion probe body.

Corrosion rates can be exacerbated due to temperature differences between the corrosion fluids and the surrounding environment. For example, in a predominantly non-aqueous solvent, small amounts of water will condense at the dew point and water-soluble salts, acids, and other corrodants may collect in that aqueous phase. This same phenomenon can occur in reverse on an evaporating metal surface. As temperatures increase, the concentration of water-soluble salts, acids, and other corrodants will increase with the evaporation of water, causing high corrosion rates. Corrosion rates generally increase with temperature, but can be complicated by various phenomenon (e.g., absorption, reaction, product/reactant transport). For example, the ability to modify the temperature within a probe can help to understand the corrosion reaction.

Moreover, the temperature of the corrosion fluid may be different in different locations within the pipe. For example, in some units, temperature variability may be high downstream. In this embodiment, the sensor 240 may be placed upstream, where variability is less, and thus a stable baseline for corrosion may be determined. Furthermore, in some embodiments, it may be difficult to place the probe in certain locations within the system, such as in a condenser, heat exchanger, or process unit. In these embodiments, the temperature of the probe may be artificially adjusted, such as through use of the heat exchanger 250 described herein, to emulate the conditions at those locations.

By having the sensor 240 be attached to a machined section of the body portion 220, the sensor 240 is physically capable of resisting heat and pressure from fluid flow through the annulus, allowing for heat exchange to take place via channels, such as channel 230, within the annulus.

The heat exchanger 250 serves to provide either heated or cooled fluid (a heat transfer medium) through the channel 230 to heat or cool the body portion 220. The heat transfer medium is pumped from an external unit into the channel 230. This insertion of the heat transfer medium allows for determination of the corrosion rate. In one example embodiment, the heat exchanger 250 is used to induce condensation artificially to the body portion 220 to emulate and/or be indicative of a cooled condition downstream or upstream from the body portion 220 location within the equipment. In another example embodiment, the heat exchanger 250 is used to induce a heated evaporated state within the body portion 220 to emulate and/or be indicative of a heated condition downstream or upstream from the body portion 220 location within the equipment.

In one instance, the heat exchanger 250 stabilizes the temperature of the sensor 240 in the body portion 220. Thus, the corrosion probe 220 may be rendered less sensitive to temperature changes within the process. The decrease in sensitivity is also due to the nature of the ultrasonic process used, as the speed of sound is not highly sensitive to temperature. In contrast, in ER probes, for example, the electrical resistivity of metals is highly sensitive to temperature. Due to their construction, ER probes are nearly useless if temperature is varying.

In some example embodiments, a temperature sensor may additionally be present on the body portion 220 to monitor the temperature of the probe. If a threshold temperature value is exceeded, the temperature sensor may send an alert and the heat exchanger may then be directed to cool the probe.

Figure 3:
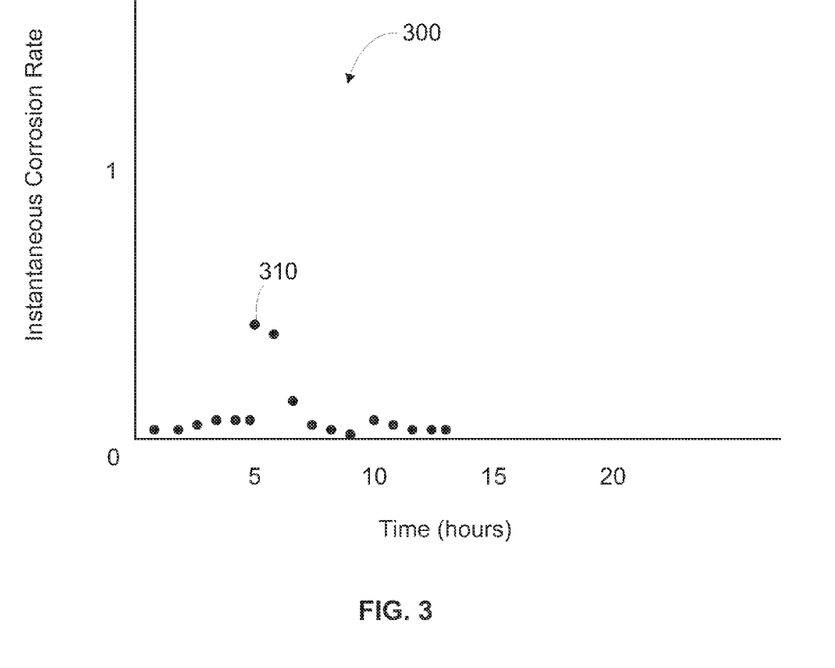
FIG. 3 depicts a graph illustrating instantaneous corrosion rate plotted over time, as may be determined using the exemplary system of FIG. 1 in accordance with at least one embodiment.

FIG. 3 depicts a graph 300 illustrating instantaneous corrosion rate plotted over time as may be measured by the system 100 of FIG. 1, in accordance with at least one embodiment. The data that comes from an ultrasonic measurement is the thickness of a surface. The change of thickness over time (the first derivative) provides a corrosion rate, such as that plotted over time in FIG. 3. Such real-time data is valuable to monitor a process and to alert operators when severe corrosion conditions exist so that process evaluations can be made. Under steady-state conditions, process variables can be optimized to achieve operational goals (e.g., tradeoff between running process "hard" and safe conditions) and economic tradeoffs between efficiency and profitability can be evaluated. Real-time data also allows operators to make informed decisions on operational constraints. For example, a decision may be made regarding whether to increase the rate of production based on the corrosion data. In another example, if recycle feeds from upstream or downstream the probe body location exceed corrosion rate targets then operators may take action to avoid exposing the upstream or downstream processes. The data shown in the example in FIG. 3 may also be used as part of mandatory reporting to show the equipment has met code. Other useful applications for data such as that shown in FIG. 3 may be envisioned.

From the data in the graph 300, from hours 1 through 4, minimal corrosion indicative of a steady state of the corrosion probe takes place, and a significant corrosion event, indicated by point 310, is observed at the 5 hour mark. Because the corrosion rate can be measured and displayed in real-time with the system 100, an operator of the system is able to take prompt measures to change the corrosive environment if needed to reduce the amount of corrosion within the process equipment. As shown in the graph 300, after detection of the corrosion event at point 310, the instantaneous corrosion rate is addressed, and it decreases to return to minimal, steady state corrosion levels.

If a corrosion event is detected, such as at point 310, a system such as system 100 may be configured to take corrosion readings and determine an instantaneous corrosion rate at a greater frequency, until a steady state condition is achieved. Existing systems do not allow one to observe the corrosion rate over a short period of time (i.e., hours or days rather than weeks or months). Instead, existing systems only allow the user to observe a very large corrosion events over a short period of time or moderate corrosion events over a long period of time. Because the present invention detects even moderate corrosion events in real-time, users are also able to look for other process anomalies near that time and can correct the cause of the anomaly.

The measurement of corrosion rate and other corrosion parameters using the system 100 may be used to monitor corrosion of a material over time, to diagnose a corrosion event, and to guide decisions to reduce or minimize environmental factors that contribute to corrosion and corrosive events.

Figure 4:
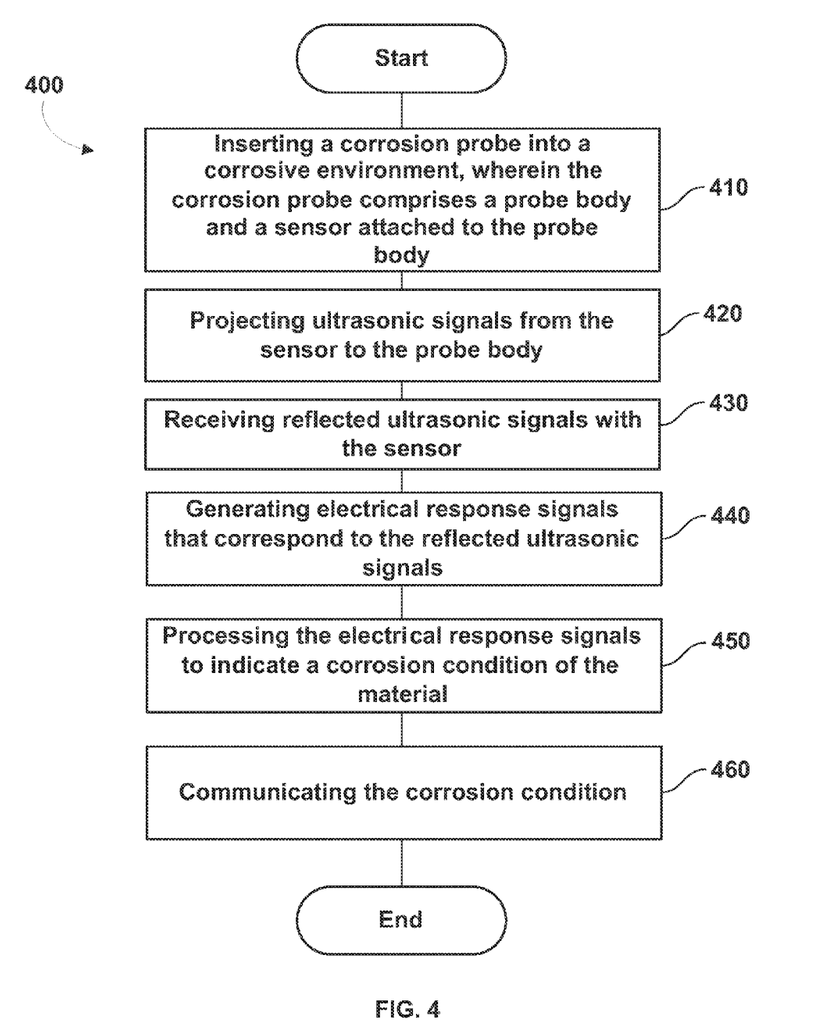
FIG. 4 depicts a simplified flow diagram of an example method that may be carried out to detect a corrosion condition of a corrodible material in a corrosive environment, in accordance with at least one embodiment.

FIG. 4 depicts a simplified flow diagram of an example method 400 that may be carried out to measure corrosion conditions in-situ, in accordance with at least one embodiment. Method 400 shown in FIG. 4 presents an embodiment of a method that, for example, could be used with the system 100.

In addition, for the method 400 and other processes and methods disclosed herein, the flowchart shows functionality and operation of one possible implementation of the present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact disc read only memory (CD-ROM), for example. The computer readable media may also be any other volatile or non-volatile storage systems. The computer readable medium may be considered a computer readable storage medium, a tangible storage device, or other article of manufacture, for example. Alternatively, program code, instructions, and/or data structures may be transmitted via a communications network via a propagated signal on a propagation medium (e.g., electromagnetic wave(s), sound wave(s), etc.).

The method 400 allows for determining a corrosion condition of a material in a corrosive environment.

Initially, the method 400 includes inserting a corrosion probe into a corrosive environment, wherein the corrosion probe comprises a probe body and a sensor attached to a machined section of the probe body, at block 410. The sensor may be a transducer. The corrosion probe may be the same or similar to the corrosion probes 140 or 200 of FIGS. 1 and 2, in one example embodiment, and may be inserted into equipment such as the pipe 110 of FIG. 1. Furthermore, the initial thickness of the pipe may be measured prior to installation in the system, or may be physically machined to produce a known thickness.

The method 400 then includes projecting ultrasonic signals from the sensor to the probe body, at block 420. Ultrasonic signals may be projected from a sensor such as the sensor 240 of FIG. 2.

The method 400 includes receiving reflected ultrasonic signals with the sensor, at block 430. A sensor such as the sensor 240 of FIG. 2 may receive the reflected ultrasonic signals.

The method 400 then includes generating electrical response signals that correspond to the reflected ultrasonic signals, at block 440. The electrical response signals may be sent from a corrosion probe, such as the corrosion probes 140 or 200 of FIGS. 1 and 2, through circuitry, such as the circuitry 150 of FIG. 1, to a processing device.

The method 400 includes processing the electrical response signals to indicate a corrosion condition of the material, at block 450. The electrical response signals may be processed using a processing device such as the processor 160 of FIG. 1.

The method 400 then includes communicating the corrosion condition, at block 460. The corrosion condition may be communicated via communication links 170, to a display or other device. The corrosion condition may include a corrosion rate, a corrosion event, or other information related to the degradation of a material. The corrosion condition may be plotted in a graph such as the graph 300 of FIG. 3 for further analysis and review.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A system for measuring corrosion rate comprising:
    a corrosion probe body for insertion within an interior of an equipment through which corrodant fluid flows, wherein the corrosion probe body comprises a material substantially identical to that of the equipment;
    a plurality of sensors on the corrosion probe body that includes an ultrasonic source configured to provide an ultrasonic signal into the probe body material, and a receiver configured to receive reflections of the ultrasonic signal from the probe body material and generate electrical response signals indicative of the travel time of the ultrasonic signal, wherein the plurality of sensors comprises at least a first sensor and a second sensor, and wherein the first sensor has a first focal point located at a first probe thickness and the second sensor has a second focal point located at a second probe thickness;
    a processor configured to process the electrical response signals and produce corresponding metal loss and corrosion data; and
    a communication unit to communicate the corresponding corrosion data to a display on an exterior surface of the material.

2. The system of claim 1, wherein the first sensor is located on a first side of the corrosion probe body and the second sensor is located on a second side of the corrosion probe body.

3. The system of claim 1, wherein the first sensor is located at a first location on the corrosion probe body and the second sensor is located at a second location on the corrosion probe body.

4. The system of claim 1, wherein the system further includes a temperature sensor to receive and collect temperature data from the temperature sensor indicative of the temperature within the equipment material, and
    wherein the system further comprises circuitry configured to send the temperature data and electrical response signals to the processor.

5. The system of claim 4, further comprising a heat-exchanger in fluid communication with an annulus within the probe body.

6. The system of claim 5, wherein the heat exchanger delivers heated fluids to the annulus to heat the probe body to an evaporating condition.

7. The system of claim 5, wherein the heat exchanger delivers cooled fluids to the annulus to cool the probe body to a condensation condition.

8. The system of claim 1, wherein the processor continuously processes the electrical response signals and produces corresponding corrosion data, and
    wherein the communication unit continuously communicates the corresponding corrosion data to the display.

9. A method for detecting a corrosion condition of a corrodible material in a corrosive environment comprising:
    inserting a corrosion sensor into the corrosive environment, wherein the corrosion sensor comprises a probe body comprised of a material substantially identical to that of the corrodible material and a plurality of sensors attached to the probe body that is capable of projecting and receiving ultrasonic signals, wherein the plurality of sensors comprises at least a first sensor and a second sensor, and wherein the first sensor has a first focal point located at a first probe thickness and the second sensor has a second focal point located at a second probe thickness;
    projecting ultrasonic signals from the sensors to the probe body;
    receiving reflected ultrasonic signals with the sensors;
    generating electrical response signals that correspond to the reflected ultrasonic signals;
    processing the electrical response signals to indicate a corrosion condition of the material; and
    communicating the corrosion condition.

10. The method of claim 9, further comprising:
    exposing the probe body to a heat exchange fluid to heat or cool the probe body.

11. The method of claim 9, wherein projecting the ultrasonic signals, receiving the reflected ultrasonic signals, generating the electrical response signals, processing the electrical response signals, and communicating the corrosion condition are performed continuously.

12. The method of claim 9, further comprising:
    receiving and collecting temperature data from a temperature sensor indicative of a temperature within the corrosive environment.

* * * * *